US00PP16550P2

(12) United States Plant Patent
Olesen

(10) Patent No.: US PP16,550 P2
(45) Date of Patent: May 16, 2006

(54) SHRUB ROSE PLANT NAMED 'POULCOT006'

(50) Latin Name: ***Rosa* hybrid**
Varietal Denomination: Poulcot006

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 73 days.

(21) Appl. No.: 11/002,530

(22) Filed: Dec. 1, 2004

(51) Int. Cl.
*A01H 5/00* (2006.01)

(52) U.S. Cl. ..... Plt./107
(58) Field of Classification Search ..... Plt./107, Plt./149, 150
See application file for complete search history.

*Primary Examiner*—Anne Marie Grunberg
*Assistant Examiner*—June Hwu

(57) ABSTRACT

A new garden rose plant of the shrub rose class which has abundant, pink flowers and attractive foliage. This new and distinct variety has shown to be uniform and stable in the resulting generations from asexual propagation.

3 Drawing Sheets

Botanical classification: *Rosa* hybrid.
Variety denomination: 'Poulcot006'.

SUMMARY OF THE INVENTION

The present invention constitutes a new and distinct variety of garden rose plant that originated from a controlled crossing between the female seed parent. 'Pouldiram' and the male pollen parent, an unnamed seedling.

The two parents were crossed during the summer of 1995, and the resulting seeds were planted in a controlled environment in Fredensborg, Denmark. The new variety is named 'Poulcot006'.

The new variety may be distinguished from its female seed parent 'Pouldiram', described in the U.S. Plant Pat. No. 12,568 issued Apr. 23, 2002, from the following combination of characteristics:

1. 'Pouldiram' produces white flowers, while 'Poulcot006' produces pink flowers.
2. 'Poulcot006' has fewer flower petals per flower than 'Pouldiram'.

The new variety may be distinguished from the male pollen parent by the following combination of characteristics:

1. The pollen parent has more flower petals per flower than 'Poulcot006'.
2. Flowers of the pollen parent are red, while flowers of 'Poulcot006' are pink.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Disease resistance;
4. Production of rose hips;

This combination of qualities is not present in previously available commercial cultivars of this type, known to the inventor, and distinguish 'Poulcot006' from all other varieties of which we are aware.

As part of the rose development program, Mogens N. Olesen germinated the seeds from the aforementioned hybridization during winter of 1995 and conducted evaluations on the resulting seedlings in a controlled environment in Fredensborg, Denmark.

'Poulcot006' was selected in the spring of 1996 by the inventor as a single plant from the progeny of the aforementioned hybridization.

Asexual reproduction of 'Poulcot006' by traditional budding and rooted cuttings was first done by Mogens N. Olesen in the nursery in Fredensborg, Denmark in July 1996. This initial and other subsequent asexual propagations conducted in controlled environments have demonstrated that the characteristics of 'Poulcot006' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcot006'. Specifically illustrated in the drawings:

FIG. 1.2; sepals, receptacle showing reproductive organs, and pedicel;

FIG. 1.3; Open flower;

FIG. 1.4; Flower petals, detached;

FIG. 1.5; Juvenile stem and foliage showing anthocyanin;

FIG. 1.6; Mature foliage;

FIG. 1.7; Bare stems exhibiting thorns;

DETAILED DESCRIPTION OF THE VARIETY

Figure 1:
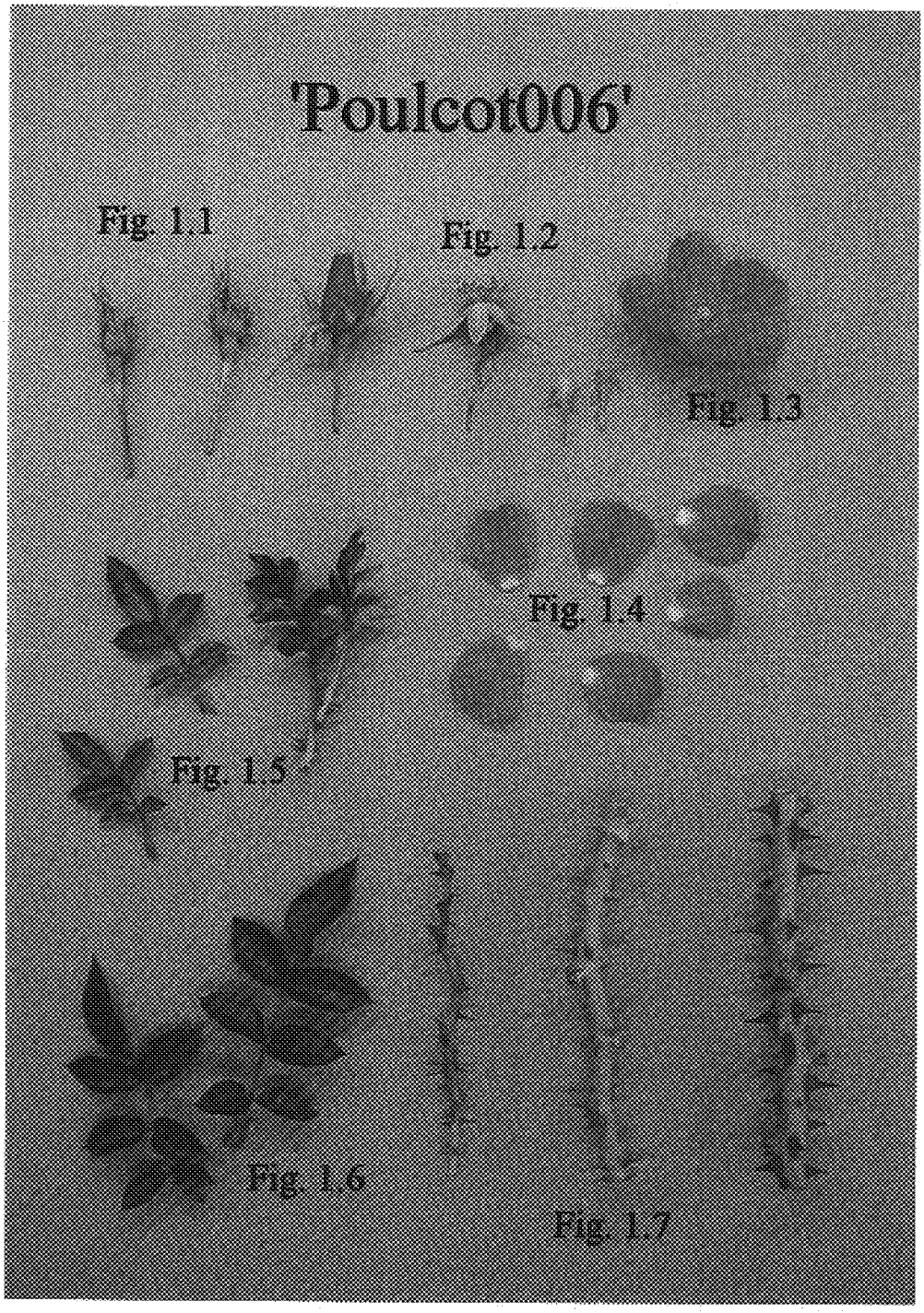
FIG. 1.1; Flower bud at various stages of development.
Figure 2:
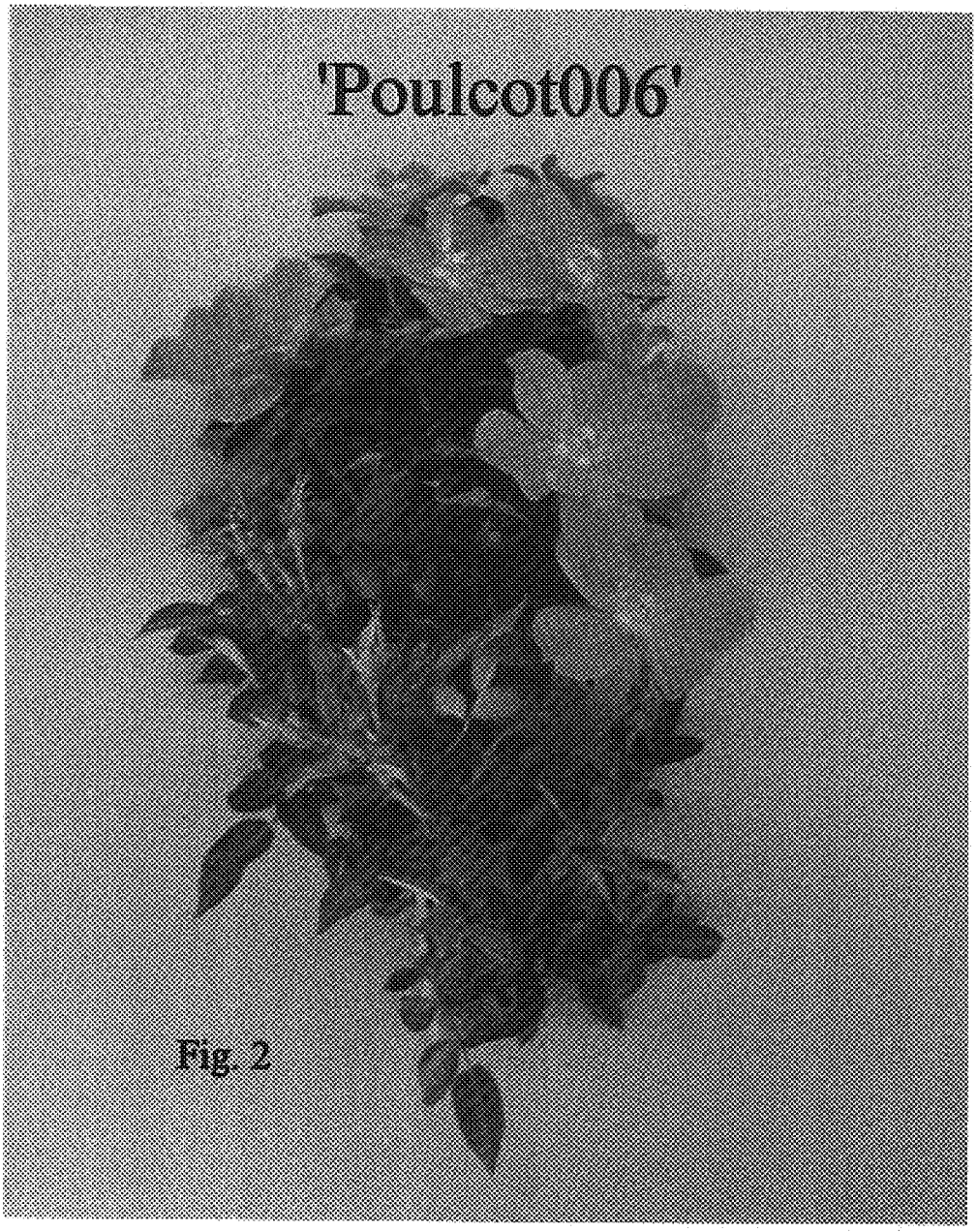
FIG. 2.1; Cluster of open flowers, leaves, and stems.
Figure 3:
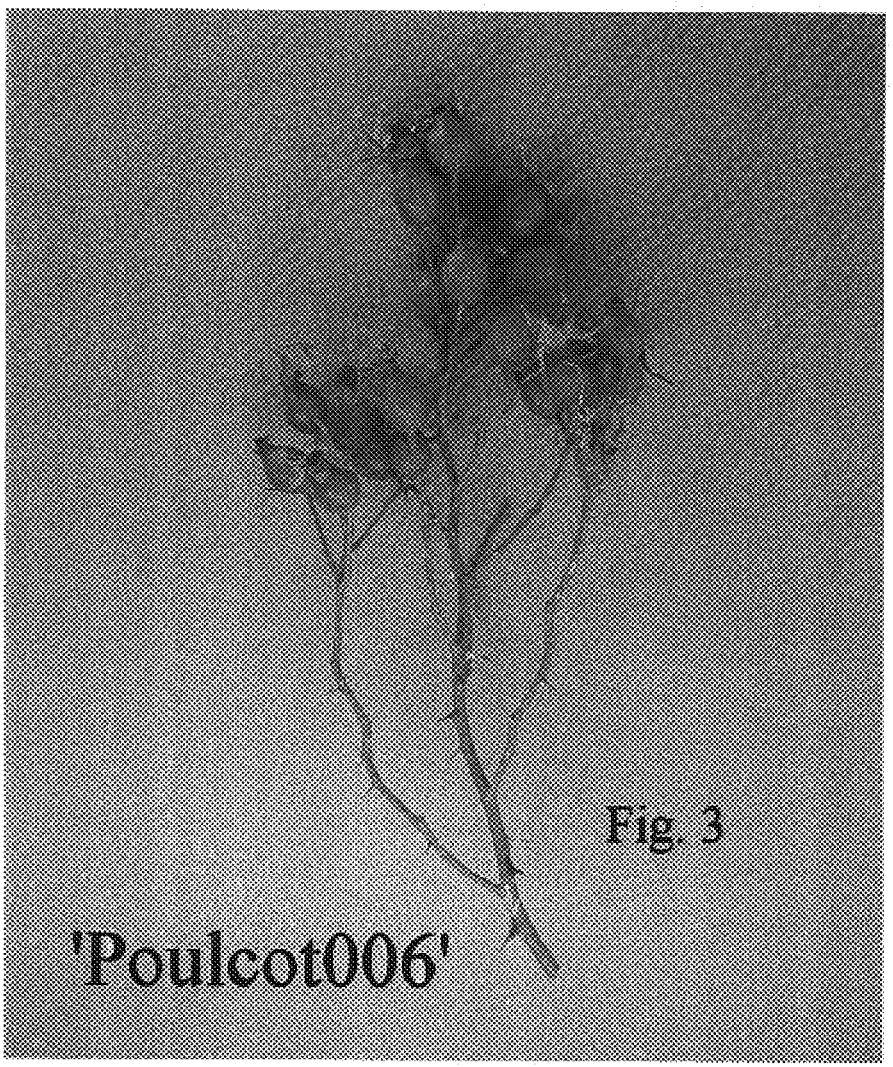
FIG. 3; Rose hips.

The following is a description of 'Poulcot006', as observed in its growth in a field nursery in Jackson County, Oreg. Observed plants are 2 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulrijk', a rose variety from the same inventors described and illustrated in U.S. Plant Pat. No. 12,519 issued Apr. 2, 2002, are compared to 'Poulcot006' in Chart 1.

CHART 1

| | 'Poulcot006' | 'Poulrijk' |
|---|---|---|
| General tonality. | Red Group 55A to Red-Purple Group 58B. | Red-Purple Group 58C. |
| Flower bud color when sepals first unfold | Red-Purple Group 58B to Red-Purple Group 57A. | Red-Purple Group 58C to D. |
| Flower bud size. | 15 mm. | 18 to 22 mm. |

FLOWER AND FLOWER BUD

Blooming habit: Continuous. Flowers profusely from May until frost.

Flower bud:

*Size.*—Upon opening, 15 mm in length from base of receptacle to end of bud. Bud diameter is 5 mm.

*Bud form.*—Ovate.

*Bud color.*—As sepals unfold, petals are Red. Purple Group 58B to Ref-Purple Group 57A.

*Sepal inner surface.*—Color: Yellow-Green Group 146C Surface: Medium pubescence observed.

*Sepal outer surface.*—Color: Yellow-Green Group 144A. Anthocyanic pigments the color of Greyed-Red 180A observed. Texture:

*Sepal shape.*—Apex: Cirrhose. Base: Flat at union with receptacle.

*Sepal margin.*—Margins have medium foliaceous appendages on three of the five sepals.

*Sepal size.*—20 mm (l)×5 mm (w).

*Receptacle.*—Texture: Smooth. Shape: Pear shaped. Size: 5 mm (h)×3 to 4 mm (w). Color: Yellow-Green Group 144A to 144B. Anthocyanic pigments the color of Greyed-Red Group 181B observed.

*Peduncle.*—Surface: Smooth. Length: 15 to 20 cm. Diameter: 6 mm on average. Color: Yellow-Green Group 146C.

*Pedicel.*—Surface: Rough with stipitate glands. Length: 20 mm on average. Diameter: 1.5 mm on average. Color: Yellow-Green Group 144B. Anthocyanic pigments Greyed-Red Group 178A. Strength: Somewhat strong.

Flower bud development: Flower buds develop in clusters of 3 to 5 flower buds per flowreing stem, occurring every 15 to 30 mm along the flowering branch. Inflorescence type is a thyrse.

Flower bloom:

*Fragrance.*—None.

*Duration.*—The blooms have a duration on the plant of approximately 5 to 8 days. Petals fall cleanly away from plant.

*Size.*—Flower diameter is 45 to 50 mm when open. Flower depth is 8 mm.

*Flower shape.*—Single, fully open and almost flat.

*Shape of flower, side view.*—Upon opening Upper portion: Flat. Lower portion: Flattened convex. After flowers open: Upper portion: Flat. Lower portion: Flattened convex.

*Petalage.*—Under normal conditions, flowers have 6 to 7 petals.

*Petal color.*—Upon opening: Upper surface: Red-Purple Group 58B with intonations of Red Group 58C to 52D. Light intonations of Orange-Red Group 32D at the basal zone. Lower surface: Red-Purple Group 58B to 58C. Basal petals spots, upon opening: Upper surface: Yellow Group 5B. Lower surface: Yellow Group 4B. After opening: Upper surface: Red-Purple Group 62A with intonations of Red-Purple Group 58B. Lower surface: Red-Purple 58B to 58C. Basal petal spots, after opening: Upper surface: Yellow Group 5C. Lower surface: Yellow Group 4D.

General tonality: On open flower Red Group 55A to Red-Purple Group 58B. After 6 to 8 days flowers fade to Red-Purple Group 62A.

Petals:

*Petal reflex.*—Flat.

*Margin.*—Entire.

*Shape.*—Generally narrow elliptical. Apex: Cuspidate. Base: Acute.

*Size.*—26 mm (l)×22 mm (w).

*Texture.*—Smooth.

*Thickness.*—Thin.

Reproductive organs:

*Pollen.*—None observed.

*Anthers.*—Size: 2 mm in length. Color: Yellow Group 12C with margins Greyed-Orange Group 163A. Quantity: 113 average.

*Filaments.*—Color: Yellow-Orange Group 17C. Length: 6 mm.

*Pistils.*—Length: 4 mm. Quantity: 31.

*Stigmas.*—Inferior in location relative to the length of the filaments and the height of the anthers. Stigmas are arranged tightly at the center. 2 to 3 cm space between stigmas and surrounding anthers. Color: Greyed-Yellow Group 161C.

*Styles.*—Color: Greyed-Red Group 181C.

*Hips.*—Color: Greyed-Orange Group 171A. Size: 15 mm (l)×13 mm (w).

PLANT

Plant growth: Spreading and low growing. When grown as a budded field grown plant on *Rosa multiflora* understock, the average height of the plant is 40 to 60 cm and the average width is 40 to 60 cm.

Stems:

*Color.*—Juvenile growth: Yellow-Green Group 145B. Anthocyanic intonations of Greyed-Red Group 181C. Mature growth: Yellow-Green Group 146C.

*Length.*—On average, canes are 20 to 40 cm from the base of the plant to the flowering portion.

*Diameter.*—4 to 5 mm.

*Internodes.*—On mature canes, there is an average distance of 20 mm between nodes.

*Surface texture.*—Young wood: Smooth. Older wood: Smooth.

Thorns:

*Incidence.*—40 thorns per 10 cm of stem on average.

*Size.*—10 mm.

*Shape.*—Upper side: Concave. Lower side: Concave.

*Color.*—Juvenile thorns: Greyed-Red Group 182A. Mature thorns: Greyed-Yellow Group 160A to Yellow-Green Group 144C.

Plant foliage.—7 leaflets on leaves in middle of the stem.

*Compound leaf.*—90 mm (l)×50 mm (w).

*Quantity.*—5 leaves per 10 cm of stem on average.

*Color of mature foliage.*—Upper side: Yellow-Green Group 147A. Lower side: Yellow-Green Group 147C to Green Group 138B.

*Color of juvenile foliage.*—Upper side: Yellow-Green Group 146A. Margins Greyed-Red Group 181A. Lower side: Yellow-Green Group 146C.

Plant leaves and leaflets:

*Stipules.*—Size: 16 to 22 mm in length. Shape: Linear, slightly broad based with outward extending apecies. Margins: Finely serrated with stipitate glands. Color: Anthocyanin: Yellow-Green Group 146A.

*Petiole.*—Length: 15 to 23 mm. Diameter: 2 mm.

*Upper surface.*—Color: Yellow-Green Group 144D.

*Lower surface.*—Color: Yellow-Green Group 146C. Observations: Stipitate glands. Small prickles.

*Rachis.*—Length: 37 mm average. Upper surface: Color: Yellow-Green Group 146A. Lower surface: Color: Yellow-Green Group 146B. Observations: Stipitate glands. Small prickles.

*Leaflet.*—Edge: Serrated. Size: Average size of the terminal leaflet on normal leaves is 30 mm (l)×17 mm (w). Shape: Ovate. Base: Obtuse. Apex: Acuminate. Texture: Smooth. Thickness: Average. Arrangement: Odd pinnate. Venation: Reticulate. Glossiness: Glossy.

Disease resistance: Above average resistance to powdery and downy mildews, rust, black spot, and Botrytis under normal growing conditions in Jackson County, Oreg.

Cold hardiness: The variety 'Poulcot006' has been found to be cold tolerant to USDA Cold Hardiness Zone 6.

What is claimed is:

1. A new and distinct variety of rose plant of the shrub rose class named 'Poulcot006', substantially as illustrated and described herein as a distinct and novel rose variety due to its abundant pink flowers, plentiful rose hips, exceptional disease resistance, and extended period of bloom.

* * * * *

'Poulcot006'
Fig. 1.1
Fig. 1.2
Fig. 1.3
Fig. 1.4
Fig. 1.5
Fig. 1.6
Fig. 1.7